(12) United States Patent
Liu et al.

(10) Patent No.: US 9,136,483 B1
(45) Date of Patent: Sep. 15, 2015

(54) THIOPHENE FUSED AZACORONENES: REGIOSELECTIVE SYNTHESIS, SELF ORGANIZATION, CHARGE TRANSPORT, AND ITS INCORPORATION IN CONJUGATED POLYMERS

(71) Applicants: Yi Liu, Fremont, CA (US); Bo He, Albany, CA (US)

(72) Inventors: Yi Liu, Fremont, CA (US); Bo He, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/688,866

(22) Filed: Apr. 16, 2015

Related U.S. Application Data (60) Provisional application No. 61/980,798, filed on Apr. 17, 2014.

(51) Int. Cl.
  *C07D 495/22* (2006.01)
  *H01L 51/00* (2006.01)
(52) U.S. Cl.
  CPC .......... *H01L 51/0071* (2013.01); *C07D 495/22* (2013.01)

(58) Field of Classification Search
  USPC .......................................................... 546/28
  See application file for complete search history.

(56) References Cited

PUBLICATIONS

He, B. B et al.: Thiophene fused azacoronenes: regioselective synthesis, self-organization, charge transport and its incorporation in conjugated polymers. Chem. of materials, vol. 26, pp. 3920-3927, 2014.*

* cited by examiner

*Primary Examiner* — Charanjit Aulakh
(74) *Attorney, Agent, or Firm* — Lawrence Berkeley National Laboratory (57) ABSTRACT

A regioselective synthesis of an azacoronene fused with two peripheral thiophene groups has been realized through a concise synthetic route. The resulting thienoazacoronene (TAC) derivatives show high degree of self-organization in solution, in single crystals, in the bulk, and in spuncast thin films. Spuncast thin film field-effect transistors of the TACs exhibited mobilities up to 0.028 $cm^2V^{-1}S^{-1}$, which is among the top field effect mobilities for solution processed discotic materials. Organic photovoltaic devices using TAC-containing conjugated polymers as the donor material exhibited a high open-circuit voltage of 0.89 V, which was ascribable to TAC's low-lying highest occupied molecular orbital energy level.

1 Claim, 8 Drawing Sheets

THIOPHENE FUSED AZACORONENES: REGIOSELECTIVE SYNTHESIS, SELF ORGANIZATION, CHARGE TRANSPORT, AND ITS INCORPORATION IN CONJUGATED POLYMERS

CROSS REFERENCE TO RELATED APPLICATIONS

This application claims priority to U.S. Provisional Application Ser. No. 61/980,798 filed Apr. 17, 2014, which application is incorporated herein by reference as if fully set forth in their entirety.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

BACKGROUND OF THE INVENTION

1. Field of the Invention

The present invention relates to the field of organic semiconductor and organic photovoltaics.

2. Related Art

Organic semiconductors with controllable molecular packing have great potential for use in high-performance electronic devices, such as organic field effect transistors (OFET) and organic photovoltaics (OPVs). Polycyclic aromatic hydrocarbons (PAHs) and heterocyclic PAHs that contain N, S and O heteroatoms in their aromatic skeletons, have a strong propensity to stack into one dimensional (1D) columns that serve as the preferred charge transport pathway. Among many heterocyclic PAHs, thiophene-fused coronenes have received increasing attention since they combine the unique electronic structure of the smallest benzenoid graphene and the excellent electronic properties of thiophene. Recently, several groups have reported multi-thiophene-annulated coronene systems, particularly the hexathienocoronene and contorted tetrathienocoronenes that have shown great self-assembly behavior and promising electronic properties. In order to incorporate these thienocoronenes into functional molecular frameworks such as polymers, it is desirable to have a bisthienocoronene system that can give rise to difunctional monomers. One of such molecular systems is the electron deficient bisthienocoronene diimide.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

In the discussions that follow, various process steps may or may not be described using certain types of manufacturing equipment, along with certain process parameters. It is to be appreciated that other types of equipment can be used, with different process parameters employed, and that some of the steps may be performed in other manufacturing equipment without departing from the scope of this invention. Furthermore, different process parameters or manufacturing equipment could be substituted for those described herein without departing from the scope of the invention.

These and other details and advantages of the present invention will become more fully apparent from the following description taken in conjunction with the accompanying drawings.

Here we present a concise synthesis of a thienoazacoronene (TAC) unit that features two fused thiophenes and two N atoms on the core, and two peripheral alkoxyl groups (Scheme 1). As shown by single crystal X-ray analysis, grazing incidence wide angle X-ray scattering (GIWAXS), and angular dependent near-edge X-ray absorption fine structure spectroscopy (AD-NEXAFS), the TACs have excellent self-organization properties, which corroborate with good field effect mobilities in spuncast films. OPV devices using a TAC-containing conjugated polymer as the donor material have a high open circuit voltage of 0.89 V, suggesting that TAC is a valuable, low highest occupied molecular orbital (HOMO) electron donor for tuning the energy levels in hole transporting polymers.

Figure 6:
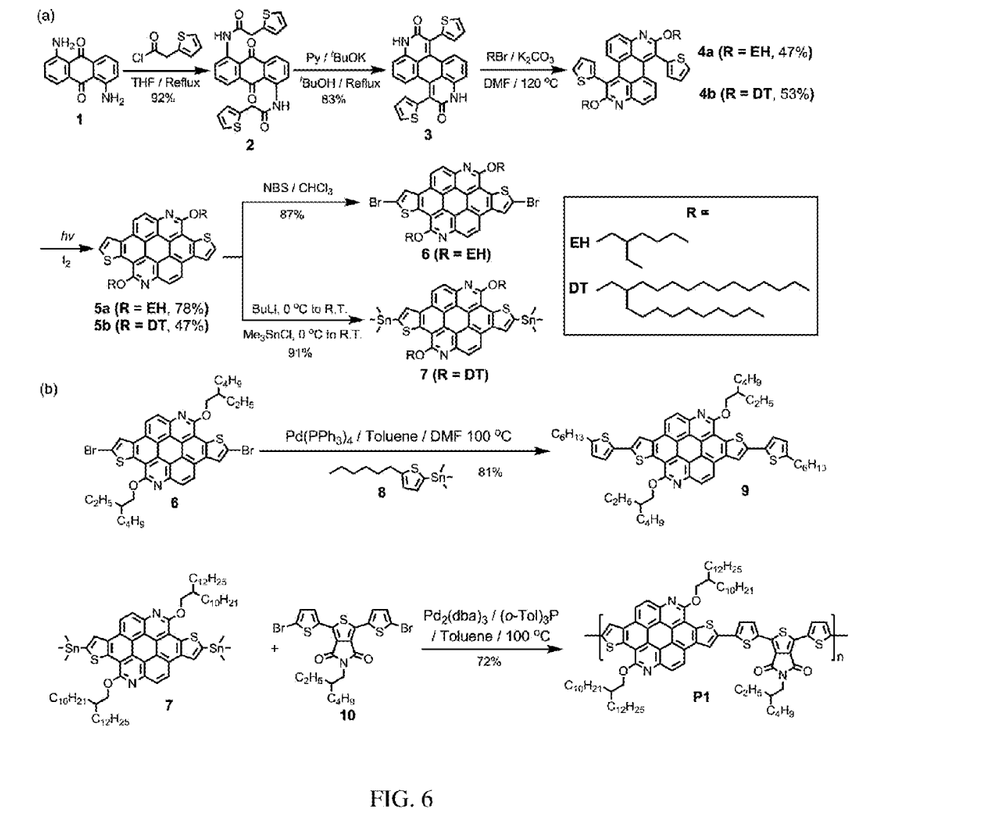
FIG. 6 illustrates a Scheme 1, the overall synthetic scheme of TAC derivatives.

The synthesis of TAC derivatives started (Scheme 1a) from acylation of commercially available 1,5-diaminoanthraquinone (1) to give the diamide 2, from which the fused 3 were obtained in 83% yield by double intramolecular Knoevenagel condensation. In the following alkylation step, the deprotonation of the amide proton went effectively in the presence of $K_2CO_3$. Thanks to an anion tautomerization (Scheme 2), O-alkylation instead of N-alkylation occurred to give the aromatized diazaperylene intermediate 4 when 2-ethylhexyl and 2-decyltetradecyl bromides were employed. Material 4 was prone to undergo thiophene-fusion reactions, and full thiophene annulation was furnished under irradiation in the presence of iodine to give 5a (EH-TAC) and 5b (DT-TAC) in 78% and 47% yield, respectively. Further functionalization of TACs was straightforward. Either bromide or trimethyltin were easily introduced to the α-position of thiophenes in high yield. Such TAC derivatives are compatible with conventional Stille coupling reaction conditions. As shown in Scheme 1b, small molecule 9 and polymer P1 were obtained in high yield after coupling 6 and 7 with a thiophene trimethylstannane and a thienopyrrolodione bromide, respectively.

Figure 1:
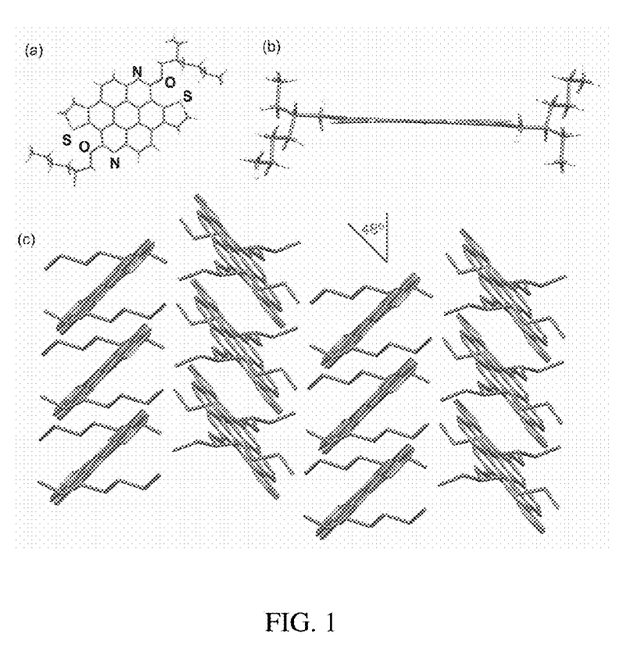
FIG. 1 illustrates a capped stick representation of X-ray structures of EH-TAC. (a) top view, (b) side view, and (c) stacked structure showing the slipped herringbone stacking (H atoms were omitted for clarity).

FIG. 1. Capped stick representation of X-ray structures of EH-TAC. (a) top view, (b) side view, and (c) stacked structure showing the slipped herringbone stacking (H atoms were omitted for clarity).

The molecular structure of 5a was unambiguously confirmed by single crystal X-ray analysis (FIG. 1), which also revealed the nearly planar conformation of the TAC core. The thiophene units slightly twisted out of the plane of azacoronene with a dihedral angle of only 2.2°. The flat TAC molecules stacked into a 1D columnar structure along the crystallographic b-axis with inter-plane spacing of 3.34 A and a centroid-to-centroid distance of 5.02 Å between two adjacent TAC cores, which suggested a slipped π-π stacking with an angle of 48° between the π stacking and the crystallographic b-axis. Accordingly, neighboring columns were arranged in a slipped herringbone stacking geometry, with nearly half of TAC's aromatic surface overlapping with the nearby ones.

Figure 2:
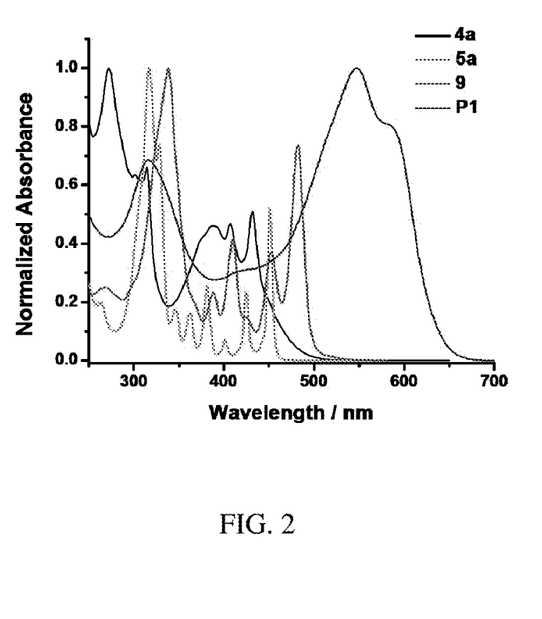
FIG. 2 illustrates UV-Vis spectra of 4a, 5a, 9 and P1 in $CHCl_3$.

Aggregation of 5a and 5b in $CDCl_3$ solution was revealed by concentration-dependent $^1H$ NMR spectroscopic changes (Figure S2 in Supporting Information, SI). The absorption spectrum of TACs displayed (FIG. 2 and Figure S4) six well-resolved absorption bands in the visible region at 451 nm, 425 nm, 402 nm, 381, 363 nm and 347 nm, together with two overlapping bands at 330 nm and 318 nm, which was very different from the spectra of the azaperylenes 4a and 4b. A linear absorption-concentration relationship, together with the lack of peak shifting in the UV-vis spectra of 5a within the concentration between 5 µM to 50 µM, indicated no aggregation at these low concentrations. In the spuncast thin film of 5a, significant peak broadening as well as bathochromic shifts of ca. 15 nm were observed, indicating molecular aggregation in the solid state. The attachment of extra thiophenes in 9 led to red shift of all the peaks. In the case of polymer P1, the fine absorption structures were replaced by broad bands. From the onset of the absorption at the lowest energy, together with electrochemical measurements using cyclic voltammetry, the optical bandgaps and frontier orbital energies could be estimated (Table 1). 5a and 5b have similar HOMO levels around −5.4 eV, which is significantly lower than the reported hexathienocoronoene (−5.08 eV) and contorted tetrathienocoronenes (−5.10 eV). The less electron-rich character of TACs can be explained by fewer fused thiophenes and the presence of two electron withdrawing N heteroatoms. P1 also has a low HOMO of -5.35 eV, which, as discussed below, is advantageous for high open circuit voltage ($V_{oc}$) in OPVs. Theoretical modeling of TAC indicates that (FIG. 8) the lowest unoccupied molecular orbital (LUMO) effectively delocalizes on the core, while the HOMO contains two nodes on C-6 and C-12.

The TACs exhibited excellent thermal stability, while differential scanning calorimetry (DSC) analysis indicated side-chain dependent metaphase transitions in 5a and 5b, with the latter having much lower melting and crystallization temperatures. Cooling from the isotropic phase of 5a resulted in a birefringent mosaic-like texture in polarized optical microscope (POM) images, which was characteristic for discotic liquid crystalline phase and also consistent with the columnar stacking in the X-ray structure 5a.

Figure 3:
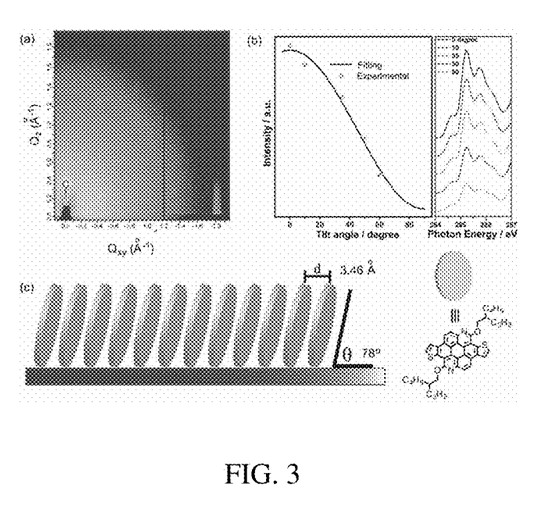
FIG. 3 illustrates (a) The GIWAXS pattern and (b) angular dependent NEXAFS of 5a. (c) Illustration of the molecular organization of 5a on surface.

The TACs showed a high order of supramolecular organization in spuncast thin films, as revealed by GIWAXS measurements (FIG. 3a). The meridional reflection in the GIWAXS pattern along $q_z$ at $q_{x,y}=0$ is related to an intercolumnar spacing of 1.76 nm. Combined with the in-plane diffraction with a d spacing of 3.46 Å, an edge-on arrangement of 5a with the column stacking parallel to the substrate can be deduced (FIG. 3c). Assuming the same π-π plane separation of 3.34 Å as in the single crystals, the aromatic cores were estimated to tilt ca 75° with respect to the substrate. This was in great agreement with the angular dependent NEXAFS measurements (FIG. 3b), from which a tilt angle of 78° between the aromatic cores and the substrate was obtained.

The preferential molecular orientation and high degree of self-organization in 5a prompted us to investigate its charge transport properties in thin film OFETs.

Hexamethyldisilazane (HMDS)-treated silicon substrates were used in bottom gate, top contact OFET devices, with thin films of 5a deposited by either evaporation or spincasting. All OFET devices exhibited p-type characteristics (Table 2). These based on spuncast, thermally annealed films perform better than the thermally deposited ones, with an average and maximum hole mobility of 0.013 $cm^2V^{-1}S^{-1}$ and 0.028 $cm^2V^{-1}S^{-1}$, respectively. Although these mobilities are notably lower than these high performing acenes and thienoacenes, they are nonetheless among the top field effect mobilities for solution processed discotic materials.

Figure 4:
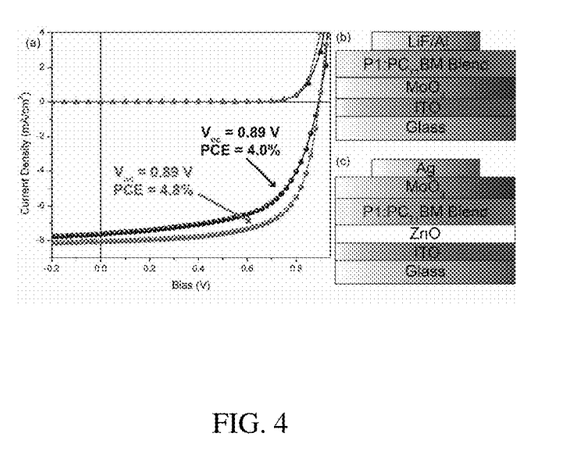
FIG. 4 illustrates (a) J-V curves of conventional (black) and inverted (red) OPVs in dark (Δ) or under illumination (•). Illustration of (b) the conventional and (c) the inverted cell architectures.
Figure 5:
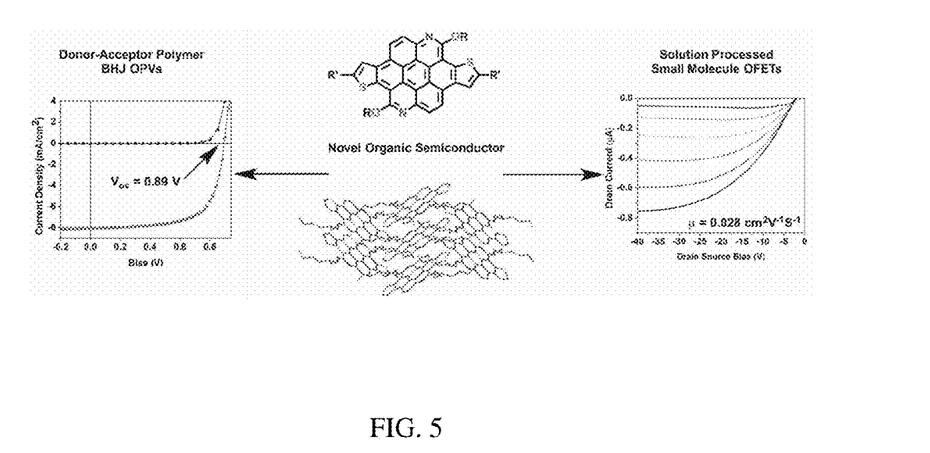
FIG. 5 illustrates results for a novel organic semiconductor.

The TAC-containing polymer P1 was tested as the donor material in bulk heterojunction solar cells (FIG. 4). The conventional OPVs displayed a maximum power conversion efficiency of 4.0%, which was further improved to 4.8% when an inverted device structure was employed. Despite the less than optimal short circuit current density, the $V_{oc}$ retained a high value of 0.89 V in both device geometries, accompanied by a fill factor up to 0.67 (Table 3). Such a high $V_{oc}$ correlates well with the low HOMO of TAC building block and the resulting P1 polymer. It affirms that TAC is a promising electron rich building block, the high chemical tunability of which allows for further optimization to give new classes of high performance conjugated polymers.

In summary, we have reported a concise and regio selective synthesis of the highly versatile thienoazacoronenes, the critical step of which utilizes an anion tautomerization to achieve simultaneous alkylation/aromatization. The incorporation of N and S heteroatoms into a PAH and the alkoxyl substitution effectively modulates the frontier orbital energy levels, which impacts $V_{oc}$ in OPVs. The thiophene-fused core undergoes easy modification at the α-position for ready integration into extended conjugated small molecules or polymers. The TACs have shown remarkable self-organization behavior in various materials states, which allow their incorporation in electronic devices such as OFETs and OPVs. The good field effect mobilities and high $V_{oc}$ underscore the great potential of TAC as a promising electron donor for the development of high performance organic electronic materials.

Figure 7:
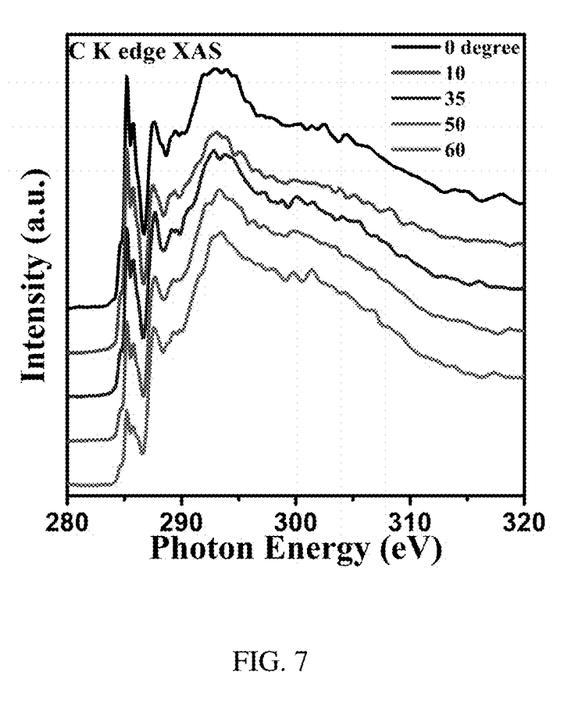
FIG. 7 illustrates C K edge XAS spectra with evolution of the tilt angle of surface normal with respect to the incident beam.

FIG. 7 illustrates C K edge XAS spectra with evolution of the tilt angle of surface normal with respect to the incident beam.

Figure 8:
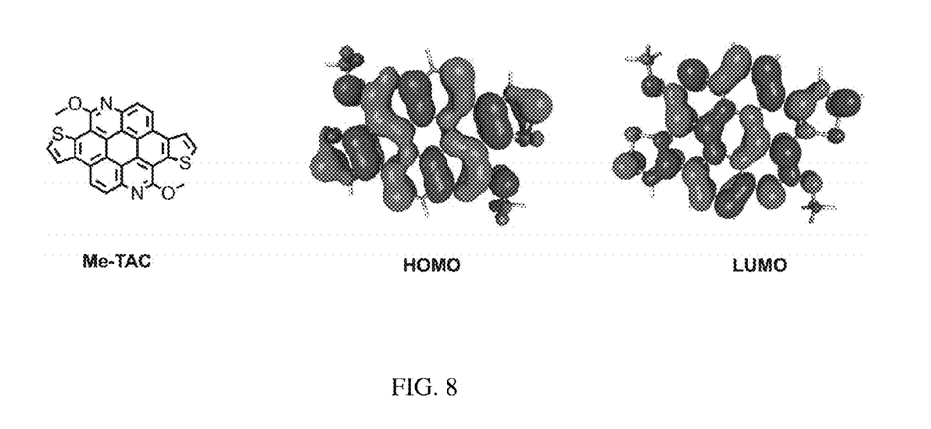
FIG. 8 illustrates the frontier orbitals of methyl-substituted TAC calculated by DFT using basis B3LYP/6-31G.

FIG. 8 illustrates the frontier orbitals of methyl-substituted TAC calculated by DFT using basis B3LYP/6-31G.

Materials and Methods

Reagents were purchased from Aldrich or synthesized as described. Prepatterned ITO-coated glass substrates were purchased from Thin Film Devices Inc. Dry solvents were collected from solvent purification system. Thin-layer chromatography (TLC) was carried out using aluminum sheets, precoated with silica gel 60F (Merck 5554). The plates were inspected by UV-light. Proton and carbon nuclear magnetic resonance spectra ($^1H$-NMR and $^{13}C$-NMR) spectra were recorded on a Bruker Avance500 II, using the deuterated solvent as lock and tetramethylsilane as internal standard. All chemical shifts are quoted using the δ scale, and all coupling constants (J) are expressed in Hertz (Hz). Matrix-assisted laser desorption ionization (MALDI) mass spectra were measured on 4800 MALDI TOF/TOF analyzer from Applied Biosystems. Thermal properties were recorded by using Q5000 Thermal Gravity Analysis (TGA) and TA Q200 Differential Scanning calorimeters (DSC). Cyclic voltammetry was performed using a 273A potentiostat (Princeton Applied Research), wherein glassy carbon, platinum and a silver wire act as the working electrode, the counter electrode and the pseudo-reference electrode, respectively. Samples were prepared in $CHCl_3$ solution with tetrabutylammonium hexafluorophosphate (0.1 M) as the electrolyte at a scan rate of 100 mV s$^{-1}$, using ferrocene/ferrocenium ($F_c/F_c^+$) redox couple as an internal standard. The HOMO levels of compounds are calculated from the difference between the first oxidation potential ($E_{oxf}$) of the compounds and the oxidation potential of ferrocene ($E_{HOMO}$=-(4.8-E) eV). The LUMO levels of compounds were calculated based on the electrochemical HOMO levels and the optical bandgap. The molecular weights were determined by PSS-WinGPC (PSS) (pump: alliance GPC 2000) GPC equipped with an RI detector using a PLgel MIXED-B column (particle size: 10 mm, dimension: 0.8×30 cm) calibrated against polystyrene standards.

UV-Vis-NIR spectra were recorded using a Cary 5000 UV-Vis-NIR spectrometer. Film thickness measurements were performed using a Dektak 150 surface profiler. The electrical characteristics of the transistors were measured using Lakeshore Probe Station model of CPX-HF and Aligent 4155C Semiconductor Parameter Analyzer at room temperature under vacuum (10$^{-3}$ Torr). A Thermal-Oriel 300W solar simulator provided an AM 1.5G solar illumination at 100 mW cm$^{-2}$ for OPV device testing. A Keithley 236 source-measure unit was used to measure current density-voltage (J-V) curves.

OPV Device Fabrication.

Conventional geometry OPVs were fabricated using a device architecture of ITO/MoO$_3$/P1:PC$_{71}$BM Blend/LiF:Al. ITO-coated glass substrates were cleaned by successive sonication in soap solution, deionized water, acetone and isopropanol for 15 min at 40° C. and UV ozone cleaned for 10 min. An ~40 nm thick PEDOT:PSS layer was prepared by spincasting its aqueous solution onto the cleaned ITO-coated glass substrate at 4000 rpm for 40 s and baked at 140° C. for 20 min before being transferred to a N$_2$ glovebox. P1 and PC$_{71}$BM were each dissolved in chloroform at a concentration of 15 mg/mL and were blended together in a 1:1 ratio prior to being spin-coated onto the PEDOT:PSS film at 1000 RPM for 30 seconds. Subsequently, the LiF (0.7 nm), and Al (100 nm) were thermally evaporated under high vacuum (~4× 10$^{-6}$ mbar) at rates of 0.2, 2 Å s$^{-1}$, respectively. The Al electrodes defined the devices with a shadow mask of 0.03 cm$^2$ in area.

Inverted OPVs were fabricated using a device architecture of ITO/ZnO/P1:PC$_{71}$BM Blend/MoO$_3$/Ag. ITO-coated glass substrates were cleaned by successive sonication in soap solution, deionized water, acetone and isopropanol for 15 min at 40° C. and UV ozone cleaned for 10 min. A 20 mM dispersion of ZnO nanoparticles in ethanol, synthesized from a reported procedure, was spin-coated onto the glass substrate at 4000 RPM for 40 s and baked at 120° C. for 10 min. The polymer blend was deposited as in the conventional geometry. Subsequently, the MoO$_3$ (8 nm), and Ag (100 nm) were thermally evaporated under high vacuum (~4×10$^{-6}$ mbar) at rates of 0.2, 2 Å s$^{-1}$, respectively. The Ag electrodes defined the devices with a shadow mask of 0.03 cm$^2$ in area.

FET Device Fabrication

Transistors were fabricated in the bottom-gate/top-contact configuration on highly doped n-type (100) Si substrates (<0.02 Ωcm) with 300-nm-thick thermally grown silicon dioxide as the dielectric layer. The Si substrates (1.6×1.4 cm$^2$) were successively ultrasonicated in soap water, water, acetone and isopropyl alcohol. Hexamethyldisilazane (HMDS) was deposited by placing the substrates in a closed crystallization dish with an open vial of HMDS for 2 hours. The capacitance per unit area of the gate dielectric layer (SiO$_2$, 300 nm) was $C_i$=11.5 nF cm$^{-2}$. The solutions were filtered through poly(tetrafluoroethylene) (PTFE, 0.45 μm) filters prior to film deposition. All the organic thin films were spuncast onto the HMDS modified Si substrates from tetrahydrofuran solutions (3 mg mL$^{-1}$) at a rotation rate of 3000 rpm for 30 s, followed by annealing at certain temperatures as noted. Sample annealing was carried out for 30 mins to 1 h, and followed by slow cooling to room temperature over 1 h. The thickness of each film was measured to be around 20-30 nm. Finally, gold source/drain electrodes (50 nm thick) were evaporated on top through a metal mask (9 pixels/chip) with channel width of 3 mm and length between 100 and 200 μm. The average mobility was obtained from a minimum of 3-9 pixels from 1-3 different chips. Scratching the SiO$_2$ dielectric layer off n-doped Si substrates provided gate electrodes. The thermal annealing was performed on a hotplate in a glovebox filled with N$_2$. All the FET measurements were performed under vacuum (10$^{-3}$ Torr) at room temperature.

General Information for GIWAXS and NEXAFS

The X-ray beam (Beamline 7.3.3, Advanced Light Source, Lawrence Berkeley National Laboratory) energy was 10 keV (lambda here is 1.24). All images were exposed using a Pilatus 1M detector to record the scattering. The angular dependence XAS experiment was performed in Beamline 8.0.1 in Advanced light source, Lawrence Berkeley National Laboratory, Berkeley, Calif. The TEY XAS signals were obtained by monitoring the offset sample current. The energy was calibration using features of C K edge XAS of HOPG.

Material Synthesis

Material 1 was purchased from Sigma-Aldrich and used without purification. Materials 8 and 10 were synthesized according to literature. Materials 2, 3, 4a, 4b, 5a, 5b, 6, 7, 9 and P1 were synthesized as described in the following synthetic procedures.

FIG. 6 illustrates a Scheme 1, the overall synthetic scheme of TAC derivatives.

2: To a stirring solution of 1,5-Diaminoanthraquinone (1, 7.00 g, 29.4 mmol, 1.0 eq) in anhydrous THF (100 mL) was added dropwise 2-thiopheneacetyl chloride (9.91 g, 61.7 mmol, 2.1 eq) under a N$_2$ atmosphere. After overnight stirring, the resulting suspension was filtered and washed with methanol. The crude product collected from filtration was further purified by recrystallization from toluene. The title compound (13.1 g, 92%) was obtained as yellow crystals. $^1$H NMR (DMSO-d6, 500 MHz): δ=12.06 (s, 2H), 8.94 (dd, J=7.4 Hz, 2.4 Hz, 2H), 7.89-7.94 (m, 4H), 7.49 (dd, J=5.1 Hz, 1.0 Hz, 2H), 7.16 (dd, J=3.4 Hz, 1.1 Hz, 2H), 7.08 (dd, J=5.1 Hz, 3.4 Hz, 2H), 4.16 (d, J=0.35 Hz, 4H). $^{13}$C NMR (DMSO- d6, 125 MHz): δ=185.75, 169.73, 152.26, 140.77, 135.91, 135.59, 134.52, 127.73, 127.19, 125.98, 125.43, 122.26, 117.48. MS (MALDI-TOF) for $C_{26}H_{18}N_2O_4S_2$: 509.32 $[M+Na]^+$.

3: A mixture of 2 (5.00 g, 10.3 mmol, 1 eq), tert-BuOK (4.61 g, 41.1 mmol, 4 eq), pyridine (9.75 g, 9.93 mL, 123.3 mmol, 12 eq) and tert-BuOH (80 mL) was refluxed for 24 h under a $N_2$ atmosphere. After the reaction was quenched with water, diluted HCl aq. was added to tune the pH to 7. The resulting precipitate was collected by filtration and washed with bulk water and acetone. The crude product was suspended in hot THF and stirred under reflux for 30 minutes. After cooling down and filtration, the title compound 2 was obtained as deep red solid (3.84 g, 83%). $^1$H NMR (DMSO-d6, 500 MHz): δ=12.09 (s, 2H), 7.74 (dd, J=5.1 Hz, 2H), 7.25 (dd, J=8.0 Hz, 2H), 7.21 (t, J=7.9 Hz, 2H), 7.16 (dd, J=3.5 Hz, 1.2 Hz, 2H), 7.08-7.11 (m, 4H). The acquisition of a $^{13}$C NMR spectrum with good signal-to-noise ratio was unsatisfactory due to limited solubility. MS (MALDI-TOF) for $C_{26}H_{14}N_2O_2S_2$: 473.26 (100%) $[M+Na]^+$.

4a: A mixture of 3 (2.70 g, 5.99 mmol, 1 eq), $K_2CO_3$ (2.48 g, 18.0 mmol, 3 eq), 18-crown-6 (catalytic) and 2-ethylhexyl bromide (3.47 g, 3.20 mL, 18.0 mmol, 3 eq) in DMF (40 mL) was heated overnight at 120° C. under $N_2$ protection. After cooling down, the excess $K_2CO_3$ was removed by filtration. The filtrate was evaporated to dryness, and the residue was subjected to chromatography column ($SiO_2$, hexanes/$CHCl_3$ 4:1 to 3:1) to yield the title product as semi-olid (1.89 g, 47%). $^1$H NMR ($CDCl_3$, 500 MHz): δ=7.72 (dd, J=8.1 Hz, 2.0 Hz, 2H), 7.51 (dd, J=5.1 Hz, 1.1 Hz, 2H), 7.48 (dd, J=7.8 Hz, 1.0 Hz, 2H), 7.32 (t, J=8.0 Hz, 2H), 7.16 (dd, J=5.1 Hz, 3.5 Hz, 2H), 7.08 (dd, J=3.5 Hz, 1.1 Hz, 2H), 4.37 (t, J=4.8 Hz, 4H), 1.69 (m, 2H), 1.29-1.38 (m, 16H), 0.92 (m, 12H). $^{13}$C NMR ($CDCl_3$, 125 MHz): δ=161.18, 146.15, 139.28, 138.81, 128.72, 128.69, 128.11, 128.07, 127.74, 127.11, 126.68, 122.93, 115.72, 68.70, 39.09, 30.72, 29.04, 24.13, 23.09, 14.14, 11.26. MS (MALDI-TOF) for $C_{42}H_{46}N_2O_2S_2$: 674.54 (100%) $[M]^+$.

4b: Synthesis of 4 was following the same synthetic procedure as 3. Yield: 53%. $^1$H NMR ($CDCl_3$, 500 MHz): δ=7.73 (dd, J=8.1 Hz, 1.0 Hz, 2H), 7.51 (dd, J=5.1 Hz, 1.1 Hz, 2H), 7.48 (dd, J=7.8 Hz, 1.0 Hz, 2H), 7.31 (t, J=8.0 Hz, 2H), 7.17 (dd, J=5.1 Hz, 3.5 Hz, 2H), 7.08 (dd, J=3.5 Hz, 1.1 Hz, 2H), 4.38 (d, J=5.3 Hz, 4H), 1.90 (m, 2H), 1.29 (m, 80H), 0.93 (m, 12H). $^{13}$C NMR ($CDCl_3$, 125 MHz): δ=161.18, 146.18, 139.28, 138.84, 128.73, 128.67, 128.09, 128.07, 127.74, 127.07, 126.68, 122.93, 115.72, 69.06, 37.57, 34.70, 34.56, 31.98, 31.64, 31.55, 30.17, 30.09, 29.76, 29.72, 29.69, 29.42, 26.84, 25.31, 22.74, 22.70, 20.72, 14.16. MS (MALDI-TOF) for $C_{74}H_{110}N_2O_2S_2$: 1122.76 $[M]^+$.

5a: A $CHCl_3$ (100 mL) solution of 4a (2.00 g, 2.96 mmol) was irradiated with a 300 W incandescent lamp in the presence of iodine for 36 h. The solution was evaporated to give a crude mixture, which was recrystallized from cyclohexane to give the title compound as yellow crystals (1.56 g, 78%). $^1$H NMR ($CDCl_3$, 500 MHz): δ=8.47 (d, J=8.7 Hz, 2H), 8.23 (d, J=8.6 Hz, 2H), 8.15 (d, J=5.3 Hz, 2H), 7.93 (d, J=5.3 Hz, 2H), 4.91 (m, 4H), 2.26 (m, 2H), 2.04 (m, 4H), 1.91 (m, 4H), 1.82 (m, 4H), 1.27 (t, J=7.5 Hz, 6H), 1.09 (t, J=7.2 Hz, 6H). $^{13}$C

NMR (CDCl$_3$, 125 MHz): δ=157.18, 139.37, 135.15, 131.19, 127.93, 126.90, 125.01, 124.2, 123.05, 121.29, 118.11, 114.21, 110.33, 69.60, 39.63, 31.02, 29.49, 24.43, 23.35, 14.37, 11.58. MS (MALDI-TOF) for C$_{42}$H$_{42}$N$_2$O$_2$S$_2$: 670.48 [M]$^+$.

5b: A CHCl$_3$ (100 mL) solution of 4b (3.50 g, 3.12 mmol) was irradiated with a 300 W incandescent lamp in the presence of iodine for 36 h. The solution was evaporated to give a crude mixture, which was purified by silica gel column to give the title compound as yellow semi-solid (1.64 g, 47%). $^1$H NMR (CDCl$_3$, 500 MHz): δ=8.44 (d, J=8.8 Hz, 2H), 8.23 (d, J=8.6 Hz, 2H), 8.14 (d, J=5.5 Hz, 2H), 7.93 (d, J=5.3 Hz, 2H), 4.93 (d, J=5.3 Hz, 4H), 2.33 (m, 2H), 2.03 (m, 4H), 1.83 (m, 4H), 1.70 (m, 8H), 1.54 (m, 8H), 1.46 (m, 8H), 1.24-1.37 (m, 46H), 0.85-0.89 (m, 12H). $^{13}$C NMR (CDCl$_3$, 125 MHz): δ=157.30, 139.48, 135.22, 131.28, 127.97, 127.01, 125.13, 124.30, 123.12, 121.33, 118.23, 114.34, 110.45, 70.03, 38.19, 31.97, 31.93, 31.88, 30.33, 29.90, 29.86, 29.82, 29.78, 29.71, 29.44, 29.40, 27.26, 22.71, 22.70, 14.12. MS (MALDI-TOF) for C$_{74}$H$_{106}$N$_2$O$_2$S$_2$: 1119.93 [M+1]$^+$.

6: To a CHCl$_3$ (100 mL) solution of 5a (1.74 g, 2.60 mmol) was added NBS (0.970 g, 5.45 mmol, 2.1 eq). The mixture was stirred overnight, after which water was added to quench the reaction. The suspension was filtrated and washed with bulk water, acetone and CHCl$_3$ to give 6 as yellow solid (1.87 g, 87%). $^1$H NMR (CDCl$_3$, 500 MHz): δ=7.75 (d, 8.5 Hz, 2H), 7.67 (d, J=8.3 Hz, 2H), 7.64 (s, 2H), 4.71 (d, J=5.5 Hz, 4H), 2.20 (m, 2H), 1.63-1.95 (m, 8H), 1.30 (t, J=7.5, 6H), 1.17 (t, J=7.2 Hz, 6H). $^{13}$C NMR of 6 was not available due to poor solubility in common solvents. MS (MALDI-TOF) for C$_{42}$H$_{40}$Br$_2$N$_2$O$_2$S$_2$: 826.28 [M]$^+$.

7: In a N$_2$ protected Schlenk flask, 5b (1.00 g, 0.890 mmol, 1.0 eq) was dissolved in anhydrous THF (20 mL). A solution of n-BuLi in hexanes (1.45 mL, 1.6 M, 2.32 mmol, 2.6 eq) was added dropwise at 0° C. After stiffing 30 minutes at 0° C., the reaction was allowed to stir at room temperature for 1h. The flask was placed into ice bath again and trimethyltin chloride in hexanes (2.68 mL, 1.0 M, 3.0 eq) was injected in one portion. The mixture was allowed to react overnight at room temperature. The reaction was treated with water and extracted with hexane. The organic phase was dried with anhydrous MgSO$_4$ and filtrated. The residue from evaporation of the filtrate was precipitated into ice-cooled methanol. Filtration gave the monomer 7 (1.17 g, 91%) as yellow solid. $^1$H NMR (CDCl$_3$, 500 MHz): δ=9.12 (d, J=8.9 Hz, 2H), 8.75 (d, J=8.7 Hz, 2H), 8.61 (s, 2H), 5.07 (d, J=5.5 Hz, 4H), 2.33 (m, 2H), 1.99-2.01 (m, 4H), 1.64-1.78 (m, 12H), 1.23-1.47 (m, 62H), 0.87 (m, 12H), 0.68 (s, 18H). $^{13}$C NMR (CDCl$_3$, 125 MHz): δ=157.96, 141.88, 139.91, 136.97, 136.80, 129.25, 127.23, 125.55, 124.60, 123.50, 119.12, 115.32, 110.89, 70.19, 38.35, 31.95, 31.93, 30.42, 29.91, 29.85, 29.80, 29.76, 29.69, 29.42, 29.37, 27.35, 22.69, 14.12, −7.92. MS (MALDI-TOF) for C$_{80}$H$_{122}$N$_2$O$_2$S$_2$Sn$_2$: 1446.76 [M]$^+$.

9: 6 (150 mg, 0.180 mmol, 1.0eq), 8 (138 mg, 0.420 mmol, 2.3 eq) and Pd(PPh$_3$)$_4$ (10.0 mg, 0.05 eq) were loaded into a 50 mL Schlenk tube. Under N$_2$ protection, toluene (6 mL) and DMF (1.5 mL) were injected into the tube. The mixture was heated to 100° C. for 24 h with stirring. The volatiles were removed under reduced pressure to give a residue, which was purified by column chromatography (SiO$_2$: hexanes/CHCl$_3$ 1:1) to give the target compound 9 as orange waxy solid (147 mg, 81%). $^1$H NMR (CDCl$_3$, 500 MHz): δ=8.19 (d, J=7.9 Hz, 2H), 8.10 (d, J=7.9 Hz, 2H), 7.82 (s, 2H), 7.21 (s, 2H), 6.81 (s, 2H), 4.88 (s, 4H), 2.96 (t, J=7.3 Hz, 4H), 2.28 (m, 2H), 2.04 (m, 4H), 1.72-1.86 (m, 16H), 1.47 (brs, 8H), 1.31 (m, 10H), 1.12 (m, 6H), 1.02 (brs, 6H). $^{13}$C NMR (CDCl$_3$, 125 MHz): δ=156.34, 145.87, 138.92, 138.63, 135.59, 135.25, 129.52, 126.25, 124.80, 124.01, 122.99, 122.25, 117.19, 115.98, 113.35, 109.27, 69.66, 39.62, 31.78, 31.66, 31.15, 30.45, 29.62, 29.11, 24.34, 23.51, 22.76, 14.49, 14.22, 11.67. MS (MALDI-TOF) for C$_{62}$H$_{70}$N$_2$O$_2$S$_2$: 1002.59 (100%) [M]$^+$.

(E) angle of the incident synchrotron beam relative to the orientation of the orbital transition dipole moment (TDM). And the resonance peak intensity appears strongest when E parallel to the orientation of TDM, and vanished when E perpendicular to TDM. So the orbital TDM orientation with respect to the substrate plane can be detected experimentally by changing the tilt angle of the sample holder. In our study, the sample holder has been tilted to get the tilt angle of sample normal with respect to the incident beam changed from 0 to 60°.

FIG. 7 illustrates C K edge XAS spectra with evolution of the tilt angle of surface normal with respect to the incident beam.

As the TMD of C 1s to π* band is perpendicular to the it stacking surface plane, i.e., the aromatic cores, so we focus on the intensities change of the features corresponding to the transition to π* band, i.e., the energy region from 284 to 287 eV. We fit the tilt angles and peaks intensities using equation 1.

P1

P1: Compound 7 (200 mg, 0.145 mmol, 1.0 eq), 10 (85.3 mg, 0.145 mmol, 1.0 eq), Pd$_2$(dba)$_3$ (4.0 mg, 0.004 mmol, 0.03 eq) and P(o-tol)$_3$ (5.3 mg, 0.017 mmol, 0.12 eq) were placed in a flame dried Schlenk tube with a stir bar and cycled vacuum/nitrogen purging three times. Dry toluene (16 mL) was then added via syringe and the reaction vessel was placed in a preheated oil bath at 100° C. and allowed to stir overnight. Bromobenzene (0.5 mL) was then added to the reaction vessel and allowed to stir for 3 hours. Then, tributylstanyl thiophene (0.5 mL) was added and the reaction was allowed to stir for further 3 hours. The reaction mixture was then cooled to room temperature and precipitated by acetone. The crude purple solid was collected by filtration, followed by sequential Soxhlet extractions with acetone, hexanes and chloroform. The chloroform fraction was passed through a silica plug to give P1 as a purple solid (162 mg, 72%). The polymer doesn't show proton resonances in C$_2$D$_2$Cl$_4$ or C$_6$D$_4$Cl$_2$ due to strong aggregation. GPC: M$_n$=20.5 kg/mol, M$_w$=113.5 kg·mol, PDI=5.53.

Discussion on angular dependent NEXAFS of 5a. NEXAFS spectra show different feature peaks as the transition from the core level initial state to unoccupied π* and σ* band. The peak intensity is determined by the electric field vector Equation 1:

$$I = A \cdot \left\{ \frac{P}{3}\left[1 + \frac{1}{2}(3\cos^2\Theta - 1)(3\cos^2\alpha - 1)\right] + \frac{(1-P)}{2}\sin^+\alpha \right\}$$

I represents the intensity of the peak, A is constant describing the absolute angle-integrated intensity, P is the degree of the X-ray beam liner polarization factor, α is the angle of the aromatic core plane tilted with respect to the substrate. Θ is the tilt angle of the substrate plane with respect to the beam (coangle of our recorded angles).

The fitting results and the energy region from 284 to 287 eV were showed in FIG. 3b in the main text. From the fitting results, we can get that the aromatic cores were tilted ca 78° with respect to the substrate.

FIG. 8 illustrates the frontier orbitals of methyl-substituted TAC calculated by DFT using basis B3LYP/6-31G*. The frontier orbitals were calculated using density functional theory at the B3YLP/6-31G* level. O-methyl substitution was used to simplify calculations.

TABLE 1

List of optical and electrochemical features of TACs in CHCl$_3$ solution.

| compound | UV-vis | | | Cyclic Voltammetry | | |
|---|---|---|---|---|---|---|
| | $\lambda_{max}{}^a$ (nm) | $\lambda_{onset}$ (nm) | $E_g{}^{opt}$ (eV) | HOMO (eV) | LUMO (eV) | $E_g{}^{electro}$ (eV) |
| 4a | 431 | 491 | 2.52 | —[b] | —[b] | —[b] |
| 4b | 432 | 491 | 2.52 | —[b] | —[b] | —[b] |
| 5a | 451 | 460 | 2.69 | −5.42[c] | −2.73[d] | n.o.[e] |
| 5b | 451 | 459 | 2.70 | −5.42[c] | −2.72[d] | n.o.[e] |
| 9 | 482 | 500 | 2.48 | −5.25[c] | −2.77[d] | n.o.[e] |
| P1 | 547 | 653 | 1.90 | −5.35[c] | −3.51[c] | 1.84[c] |

[a] The absorption maximum of the peak at the longest wavelength.
[b] not measured.
[c] Determined by cyclic voltammetry.
[d] LUMOs were estimated by LUMO = HOMO + $E_g{}^{opt}$.
[e] not observed.

TABLE 2

Summary of transfer characteristics of 5a-based OFETs fabricated at different conditions.

| Compound 5a | $\mu_h{}^{avg}$ cm$^2$V$^{-1}$s$^{-1}$ | $\mu_h{}^{dev}$ cm$^2$V$^{-1}$s$^{-1}$ | $\mu_h{}^{max}$ cm$^2$V$^{-1}$s$^{-1}$ | $V_{th}$ | $I_{On}/I_{Off}$ |
|---|---|---|---|---|---|
| Evaporated (As Cast) | 4.88 × 10$^{-3}$ | 8.25 × 10$^{-4}$ | 6.02 × 10$^{-3}$ | −13 | 10$^3$–10$^4$ |
| Evaporated (Annealed)[a] | 6.84 × 10$^{-3}$ | 1.76 × 10$^{-3}$ | 8.56 × 10$^{-3}$ | −7 | 10$^4$ |
| Spincast (As Cast) | 2.59 × 10$^{-3}$ | 1.39 × 10$^{-3}$ | 3.95 × 10$^{-3}$ | −17 | 10$^3$ |
| Spincast (Annealed)[a] | 1.25 × 10$^{-2}$ | 5.61 × 10$^{-3}$ | 2.81 × 10$^{-3}$ | −13 | 10$^4$ |

[a] All films annealed at 175° C. for 1 hour.

TABLE 3

Device characteristics of P1-based OPVs.

| Cell type | Jsc (mA/cm$^2$) | Voc (V) | Fill Factor | R-Series (Ω cm$^2$) | R-Shunt (Ω cm$^2$) | PCE |
|---|---|---|---|---|---|---|
| Conventional (average) | 6.58 | .86 | 0.58 | 1.47 | 3.65 * 10$^6$ | 3.30% |
| Conventional (Max) | 7.64 | .89 | 0.60 | 1.30 | 1.20 * 10$^7$ | 4.07% |
| Inverted (Average) | 7.08 | .89 | 0.64 | 2.25 | 1.38 * 10$^6$ | 3.98% |
| Inverted (Max) | 8.06 | .89 | 0.67 | 1.40 | 8.10 * 10$^5$ | 4.82% |

Scheme 2. The proposed mechanism for based-promoted tautomerization and alkylation.

Scheme 2. The proposed mechanism for base-promoted tautomerization and alkylation.

What is claimed is:
1. A Compound of the formula:

* * * * *